United States Patent
Nagler et al.

[11] Patent Number: 6,159,488
[45] Date of Patent: Dec. 12, 2000

[54] INTRACORONARY STENTS CONTAINING QUINAZOLINONE DERIVATIVES

[75] Inventors: Arnon Nagler, Jerusalam; Eli Hazum, Rehovot; Ehud Geller, Herzelia; Shimon Slavin, Jerusalem; Israel Vlodavsky, Mevaseret Zion; Mark Pines, Rehovot, all of Israel

[73] Assignees: Agricultural Research Org. Ministry of Agriculture (Gov.); HadasitMedical Research Serv. & Devel. Ltd., both of Israel

[21] Appl. No.: 09/325,198

[22] Filed: Jun. 3, 1999

Related U.S. Application Data

[63] Continuation-in-part of application No. 09/180,498, Mar. 29, 1999, which is a continuation of application No. PCT/US97/15254, Aug. 14, 1997.

[51] Int. Cl.[7] .................................................. A61K 31/505
[52] U.S. Cl. .......................... 424/423; 424/422; 424/424; 424/473; 514/259
[58] Field of Search .................................... 424/422, 473, 424/423, 424; 514/259

[56] References Cited

U.S. PATENT DOCUMENTS

| | | | |
|---|---|---|---|
| 3,320,124 | 5/1967 | Waletzky et al. | 167/53 |
| 4,340,596 | 7/1982 | Schein | 424/251 |
| 5,449,678 | 9/1995 | Pines et al. | 514/259 |
| 5,593,417 | 1/1997 | Rhodes | 606/191 |
| 5,653,727 | 8/1997 | Wiktor | 606/195 |
| 5,891,879 | 4/1999 | Nagler et al. | 514/259 |

FOREIGN PATENT DOCUMENTS

| | | | |
|---|---|---|---|
| 0701802 | 3/1996 | European Pat. Off. | A61F 2/06 |
| WO9606616 | 3/1996 | WIPO | A61K 31/505 |

OTHER PUBLICATIONS

Choi et al., "Halofuginone, A Specific Collagen Type I Inhibitor, Reduces Anastomotic Intimal Hyperplasia." Archives of Surgery, (1995) vol. 130/3: pp. 257–261.

Pines et al., "Halofuginone Hydrobromide." Drugs of the future., (1996) vol. 21/6: pp. 596–599.

Nyska et al., "Topically Applied Halofuginone, An Inhibitor of Collagen Type I Transcription, Reduces Peritendinous Fibrous Adhesions Following Surgery." Connective Tissue Research (1996), vol. 34(2): pp. 97–103.

Granot et al., "Halofuginone: An inhibitor of collagen type I synthesis." Biochimica et Biophysica Acta, (1993) vol. 1156, pp. 107–112.

Lindner et al., "Role of Basic Fibroblast Growth Factor in Vascular Lesion Formation." Circulation Research, (1991), vol. 68(1), pp. 106–113.

*Primary Examiner*—S. Mark Clardy
*Assistant Examiner*—Kathryne E. Shelborne
*Attorney, Agent, or Firm*—Davidson, Davidson & Kappel, LLC

[57] ABSTRACT

The invention provides an intracoronary stent coated with a quinazolinone derivative of formula (I), wherein n is 1 or 2, $R_1$ is a member of the group consisting of hydrogen, halogen, nitro, benzo, lower alkyl, phenyl and lower alkoxy; $R_2$ is a member of the group consisting of hydroxy, acetoxy and lower alkoxy, and R3 is a member of the group consisting of hydrogen and lower alkenoxy-carbonyl, and physiologically acceptable salts thereof, for preventing restenosis after angioplasty.

2 Claims, 8 Drawing Sheets

INTRACORONARY STENTS CONTAINING QUINAZOLINONE DERIVATIVES

This application is a continuation-in-part of U.S. Ser. No. 09/180,498 entitled "Intracoronary Stents Containing Quinazolinone Derivatives" filed Mar. 29, 1999, and a continuation of PCT/US97/15254 filed Aug. 14, 1997 the entire disclosure of which is hereby incorporated by reference.

FIELD OF THE INVENTION

The present invention relates to intracoronary stents coated with compositions containing quinazolinones. More particularly, the present invention relates to a stent coated with a composition for the inhibition of restenosis, comprising a quinazolinone derivative as herein defined as active ingredient therein.

The present invention is a modification of and improvement on the invention described in Israel Specification No. 110,831, the teachings of which are incorporated herein for background purposes only.

BACKGROUND OF THE INVENTION

In U.S. Pat. No. 3,320,124, issued in 1967, there is described and claimed a method for treating coccidiosis with quinazolinone derivatives.

Halogufinone, otherwise known as 7-bromo-6-chloro-3-[3- (3-hydroxy-2-piperidinyl)-2-oxopropyl]-4(3H)-quinazolinone, was first described and claimed in said patent by American Cyanamid Company, and was the preferred compound taught by said patent and the one commercialized from among the derivatives described and claimed therein.

Subsequently, U.S. Reissue Patent No. 26,833 and U.S. Pat. Nos. 4,824,847; 4,855,299; 4,861,758 and 5,215,993 all relate to the coccidiocidal properties of halofuginone, while U.S. Pat. No. 4,340,596 teaches that it can also be used for combatting theileriosis.

In U.S. Pat. No. 5,449,678, there is described and claimed an anti-fibrotic composition, comprising an amount of a compound of formula I:

wherein:
  n is 1 or 2;
  $R_1$ is a member of the group consisting of hydrogen, halogen, nitro, benzo, lower alkyl, phenyl and lower alkoxy;
  $R_2$ is a member of the group consisting of hydroxy, acetoxy, and lower alkoxy, and
  $R_3$ is a member of the group consisting of hydrogen and lower alkenoxy-carbonyl;
and physiologically acceptable salts thereof, effective to inhibit collagen type I synthesis, as active ingredient therein.

After further research and development, it was discovered that the above-identified compounds of formula I are effective in the inhibition of restenosis, which formally is not a fibrotic condition.

The pathogenesis of atherosclerosis involves abnormal migration and proliferation of smooth muscle cells (SMCs) infiltrated with macrophages and embedded in extracellular matrix (ECM) of adhesive glycoproteins, proteoglycans and collagens [V. Fuster, et al., "The Pathogenesis of Coronary Artery Disease and the Acute Coronary Syndromes," *New Eng. J. Med.,* Vol. 326, pp. 242–250 (1992); R. Ross, "The Pathogenesis of Atherosclerosis: A Perspective for the 1990's," *Nature,* Vol. 362, pp. 801–809 (1993)]. Under physiological conditions, the majority of arterial SMCs remains in the Go phase and cell growth is controlled by a balance between endogenous proliferation-stimulating and proliferation-inhibiting factors. Following endothelial cell perturbation due to atherogenic risk factors (i.e., hypertension, hyperlipoproteinemia, diabetes mellitus), platelets and non-platelet-derived growth factors and cytokines are released and stimulate monocyte and SMC migration as well as SMC proliferation (V. Fuster, et al., ibid.; R. Ross, ibid.). Among these growth factors are platelet-derived growth factor (PDGF) [G. A. A. Ferns, et al., "Inhibition of Neoinitmal Smooth Muscle Accumulation after Angioplasty by an Antibody to PDGF," *Science,* Vol. 253, pp. 1129–1132 (1991)], basic fibroblast growth factor (bFGF) [V. Lindner, et al., "Role of Basic Fibroblast Growth Factor in Vascular Lesion Formation," *Circ. Res.,* Vol. 68, pp. 106–113 (1991)], and interleukin-1 (IL-1) [H. Loppnow and P. Libby, "Proliferating or Interleukin-1 Activated Human Vascular Smooth Muscle Cells Secrete Copious Interleukin 6," *J. Clin. Invest.,* Vol. 85, pp. 731–738 (1990)]. Macrophages and platelets also release enzymes, i.e., elastase, collagenase, heparanase) that digest various constituents of the ECM and release bFGF and possibly other growth factors (TGFb) that are stored in basement membranes and ECM [I. Vlodavsky, et al., "Extracellylar Matrix-bound Growth Factors, Enzymes and Plasma Proteins," in: *Molecular and Cellular Aspects of Basement Membranes, Monographs in Cell Biology,* D. H. Rohrbach and R. Timpl, Eds., Academic Press, New York, N.Y., U.S.A., pp. 327–346 (1993)]. A potent growth-promoting activity towards SMCs is also exerted by thrombin, which, under certain conditions, may be present within the vessel wall [R. Bar-Shavit, et al., "Thrombin Immobilized to Extracellular Matrix Is a Mitogen for Vascular Smooth Muscle Cells: Non-Enzymatic Mode of Action," *Cell Reg.,* Vol. 1, pp. 453–463 (1990); S. M. Schwartz, "Serum-Derived Growth Factor is Thrombin?" *J. Clin. Invest.,* Vol 91, p. 4 (1993)]. Molecules that interfere with the growth-promoting activity of these growth factors may attenuate the progression of the atherogenic process.

Proliferation of arterial smooth muscle cells (SMC) in response to endothelial injury is a basic event in the process of restenosis of coronary arteries after percutaneous transluminal coronary angioplasty (PTCA) [V. Fuster, et al., ibid.]. Coronary bypass surgery or angioplasty are applied to reopen coronary arteries that have been narrowed by heart disease. A major problem with both procedures in that arteries rapidly reclog in about 30% of patients undergoing antioplasty and about 10% bypass surgery patients. Vascular SMC are ordinarily protected by the smooth inner lining of the arteries, composed of vascular endothelial cells. However, following bypass surgery or angioplasty, SMC are often left exposed. In a futile effort to repair the wound, the cells proliferate and clog the artery.

According to the invention claimed in Israel Specification No. 110,831, there is provided a pharmaceutical composition comprising a compound of formula I as hereinbefore defined, in a pharmaceutically effective amount for preventing restenosis by the inhibition of vascular smooth cell proliferation and in combination with a pharmaceutically acceptable carrier.

In preferred compositions of said invention, said compound is halofuginone.

As is known, conventional balloon angioplasty, introduced over 15 years ago, remains hampered by the persistence of two vexing problems: abrupt vessel closure during intervention and restenosis during follow-up. Mechanical intervention with intracoronary stents was introduced for human clinical investigation already in 1986, and following FDA approval of the first coronary stent for prevention of restenosis following balloon angioplasty, the market for the devices has grown from $220 million in 1994 to one that is expected to capture as much as $1 billion in world-wide revenues in 1996 [W. Diller, "Technology Strategies—Coronary Stents: Breaking J&J's Lock on the Market," *Start-Up*, pp. 20–26 (May 1996)].

According to said article, while angioplasty alone may result in restenosis rates of 40% or more, some studies indicate that angioplasty, followed by stent deployment, reduces the rate to 20–30%, depending on the kind and location of disease.

Obviously, a restenosis rate of 20–30% is also undesirable, and therefore it has been suggested in the literature, and there are now manufactured and sold, stents which are coated with materials designed to reduce restenosis. Thus, e.g., Johnson & Johnson International Systems markets a heparin-coated form of the Palmaz-Schartz stent and Medtronic Interventional Vascular markets a fibrin-coated Wiktor stent. Stents coated with an antithrombogenic silicon-carbide material have been sold by Biotronik GmbH, and other suggestions include the coating of metallic stents with polymers to diminish their thrombogenic properties, with a nylon mesh, and with a medical grade silicon polymer. Drug-eluting polymer coatings have also been reported [see, e.g., Tao Peng, et al., "Role of Polymers in Improving the Results of Stenting in Coronary Arteries," *Biomaterials* 1996, Vol. 17, No. 7, pp. 685–694 (1996)]. Thus, said article teaches that polymer stents can incorporate or bind drugs for later local controlled delivery at the target site that would inhibit thrombus formation and neointimal proliferation and that local administration of various drugs, including urokinase, heparin, taxol, hirudin and peptide, is being investigated to prevent thrombosis and restenosis.

SUMMARY OF THE INVENTION

With the above state of the art in mind, it has now been realized that the compositions taught in Israel Specification 110,831 can be utilized in an especially effective manner by incorporating the same as a coating on intracoronary stents, by methods known per se.

Thus, according to the present invention, there is provided an intracoronary stent coated with a quinazolinone derivative of formula I:

wherein:

$R_1$ is a member of the group consisting of hydrogen, halogen, nitro, benzo, lower alkyl, phenyl and lower alkoxy;

$R_2$ is a member of the group consisting of hydroxy, acetoxy, and lower alkoxy, and $R_3$ is a member of the group consisting of hydrogen and lower alkenoxy-carbonyl;

for preventing restenosis after angioplasty.

As indicated above, while described, exemplified and illustrated herein, the subject matter of Israel Specification No. 110,831 does not constitute a part of the present invention, and is specifically disclaimed.

With specific reference now to the examples in detail, it is stressed that the particulars described are by way of example and for purposes of illustrative discussion of the preferred embodiments of the present invention only, and are presented in the cause of providing what is believed to be the most useful and readily understood description of the principles and conceptual aspects of the invention. In this context, it is to be noted that only subject matter embraced in the scope of the claims appended hereto, whether in the manner defined in the claims or in a manner similar thereto and involving the main features as defined in the claims, is intended to be included in the scope of the present invention, while subject matter of Israel Specification 110,831, although described and exemplified to provide background and better understanding of the invention, is not intended for inclusion as part of the present invention.

EXAMPLES

1) Experimental Procedures

Cells

SMC were isolated from the bovine aortic media as previously described [see, e.g., J. J. Castellot, et al., "Structural Determinants of the Capacity of Heparin to Inhibit the Proliferation of Vascular Smooth Muscle Cells: Evidence for a Pentasaccharide Sequence that Contains a 3-0-Sulfate Group," *J. Cell Biol.*, Vol. 102, pp. 1979–1984 (1986); and A. Schmidt, et al., "The Antiproliferative Activity of Arterial Heparan Sulfate Resides in Domains Enriched with 2-0-Sulfated Uronic Acid Residues," *J. Biol. Chem.*, Vol. 267, pp. 19242–19247 (1992)].

Briefly, the abdominal segment of the aorta was removed and the fascia cleaned away under a dissecting microscope. The aorta was cut longitudinally, and small pieces of the media were carefully stripped from the vessel wall. Two or three such strips, with average dimensions of 2–3 mm, were placed in 100 mm tissue culture dishes containing DMEM (4.5 g glucose/liter), supplemented with 10% FCS, 100 U/ml penicillin and 100 mg/ml streptomycin. Within 7–14 days, large patches of multilayered cells migrated from the explnts. Approximately 1 week later, the cells were subcultured into 100-mm tissue culture plates (4–6×10$^5$ cells/plate). The cultures (passage 3–8) exhibited typical morphological characteristics of vascular SMC and the cells were specifically stained with monoclonal antibodies that selectively recognize the muscle form of actin (HF-35). This antibody does not recognize endothelial cells or fibroblasts.

Cultures of vascular endothelial cells were established from bovine aorta, as previously described by D. Gospodarowicz, et al. ["Clonal Growth of Bovine Endothelial Cells: Fibroblast Growth Factor as a Survival Agent," *Proc. Natl. Acad. Sci. U.S.A.*, Vol. 73, p. 4120 (1979)]. Stock cultures were maintained in DMEM (1 g glucose/liter) supplemented with 10% calf serum, 50 U/ml penicillin, and 50 mg/ml streptomycin at 37 dC in 10% $CO_2$ humidified incubators. Partially purified brain-derived bFGF (100 ng/ml) was added every other day during the phase of active cell growth [D. Gospodarowicz, et al., ibid., and J. Vlodavsky, et al., "Vascular Endothelial Cells Maintained in the Absence of Fibroblast Growth Factor Undergo Structural and Functional Alterations That Are Incompatible with Their In Vivo Differentiated properties," *J. Cell Biol.*, Vol 83, pp. 468–486 (1979)].

Cell Proliferation: $^3$H-Thymidine Incorporation

SMCs were plated ($4 \times 10^4$ cells/16 mm well) in DMEM supplemented with 10% FCS. 24 hours after seeding, the medium was replaced with medium containing 0.2% FCS, and 48 hours later, the cells were exposed to growth stimulants and $^3$H-thymidine (1 mCi/well) for an additional 24–48 hours. DNA synthesis was assayed by measuring the radioactivity incorporated into trichloroacetic acid insoluble material [M. Benezra, et al., "Reversal of bFGF Autocrine Cell Transformation by Aromatic Anionic Compounds," *Cancer Res.*, Vol. 52, pp. 5656–5662 (1992)].

Growth Rate

SMCs ($1.5 \times 10^4$ cells/well) were seeded into 24 well culture plates and exposed to growth stimulants as described above. 1 to 6 days after seeding, the cells were fixed with 2.5% formaldehyde in PBS. The plates were immersed in a bath of 0.1 M borate buffer (pH 8.5), stained (1 h, 24 dC) with methylene blue (1% in 0.1 M borate buffer, pH 8.5) andwashed four times in water. This procedure removed practically all non-cell-bound dye. Specific cell incorporated methylene blue was dissolved with 0.5 ml of 0.1 N HCl (1 h, 25 dC) and determined by measuring the absorbency at 620 nm (Bar-Shavit, et al., ibid.). The initial cell plating density was chosen to ensure a linear relationship between cell number and absorbance at the end of the experiment. In each experiment, 3 wells were fixed before adding the test compound to determine the initial average absorbance. This value was used to calculate doubling times (DT) of control and drug-treated cells, using the following equation:

$$DT = \ln 2 / \ln[(OD_t/OD_c)/h]$$

wherein:
DT=doubling time in hours;
$Od_t$=optical density of a test well at the end of the experiment;
$Od_c$=optical density of a control well at the beginning of the experiment;
h=duration of incubation in hours.

The growth rate was calculated by dividing the doubling time of drug-treated cells by that of control cells [A. Horowitz, et al., "In Vitro Cytotoxicity of Liposome—Encapsulated Doxorubicin: Dependence on Liposome Composition and Drug Release," *Biochim. Biophys. Acta*, Vol. 1109, pp. 203–209 (1992)].

Cell Number

SMCs were seeded ($2.5 \times 103$ cells/well) into 24-well plates in DMEM (4.5 g glucose/liter), supplemented with 10% FCS and allowed to attach for 6 hours [A. Schmidt, et al., "The Antiproliferative Activity of Arterial Heparan Sulfate Resides in Domains Enriched with 2-0-Sulfated Uronic Acid Residues," *J. Biol. Chem.*, Vol. 267, pp. 19242–19247 (1992)]. The medium was removed and experimental medium (with or without halofuginone) containing 10% FCS was added to quadruplicate wells. After 4 days of incubation, the cell number was determined, using a Coulter counter (Schmidt, et al., ibid). The degree of inhibition was calculated from the following formula:

% Inhibition=1-net growth in presence of halofuginone/net growth in control×100

The net growth was determined by subtracting the initial cell number from the final cell number.

2) Experimental Results i) Antiproliferative Effect of Halofuginone toward Vascular SMC Growth Rate Sparsely seeded vascular SMC were exposed to 10% FCS in the absence and presence of increasing concentrations of halofuginone. The cells were dissociated with STV and counted daily. As shown in FIG. 1, 80–90% inhibition of SMC proliferation was obtained in the presence of 75 ng/ml halofuginone, with an almost complete inhibition at 125 ng/ml.

Figure 1:
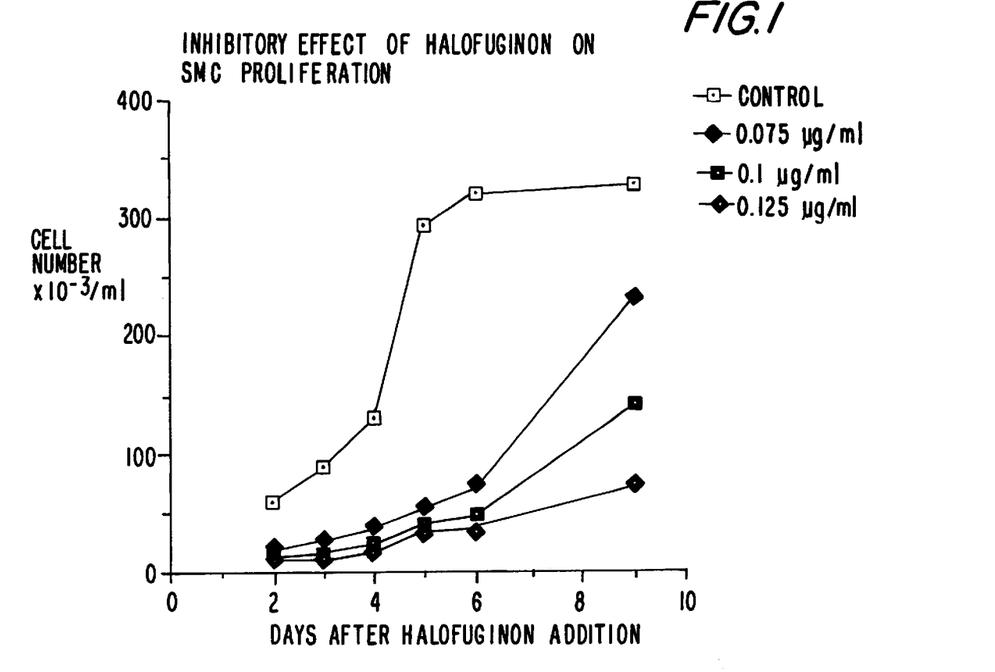
FIG. 1 is a characteristic curve showing the inhibitory effect of halofuginone on SMC proliferation.
Figure 2:
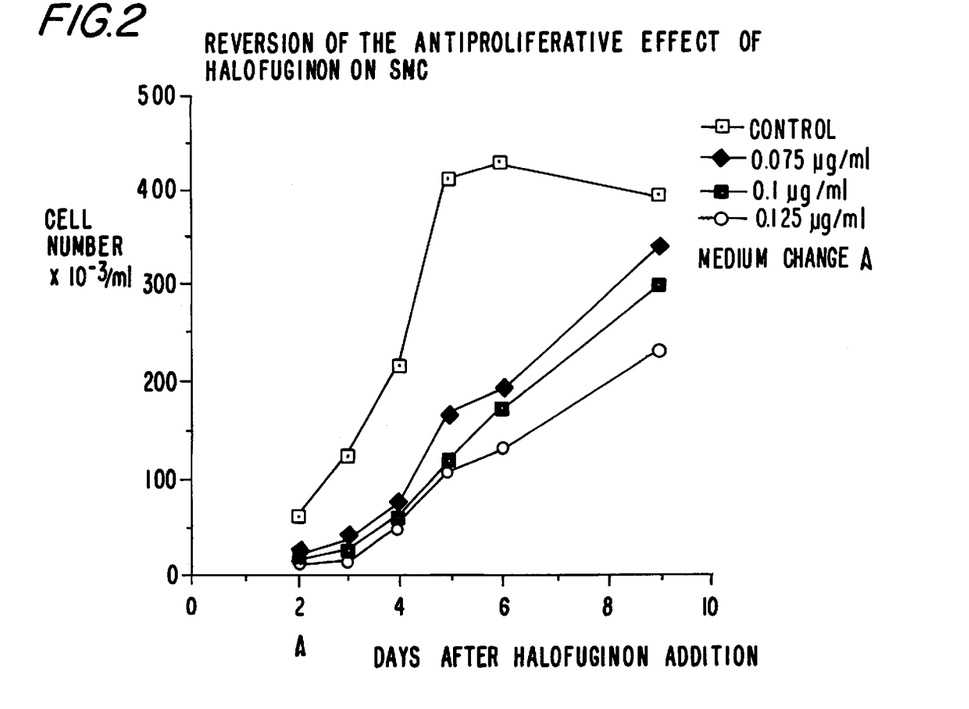
FIG. 2 is a characteristic curve showing reversion of the antiproliferative effect of halofuginone on SMC.

In another experiment, the SMCs were exposed to halofuginone for 48 hours, followed by removal of the drug and subsequent growth in regular growth medium. As demonstrated in FIG. 2, removal of the drug resulted in a gain of an accelerated growth rate similar to that of the untreated SMCs.

$^3$H-Thymidine Incorporation

Figure 3A:
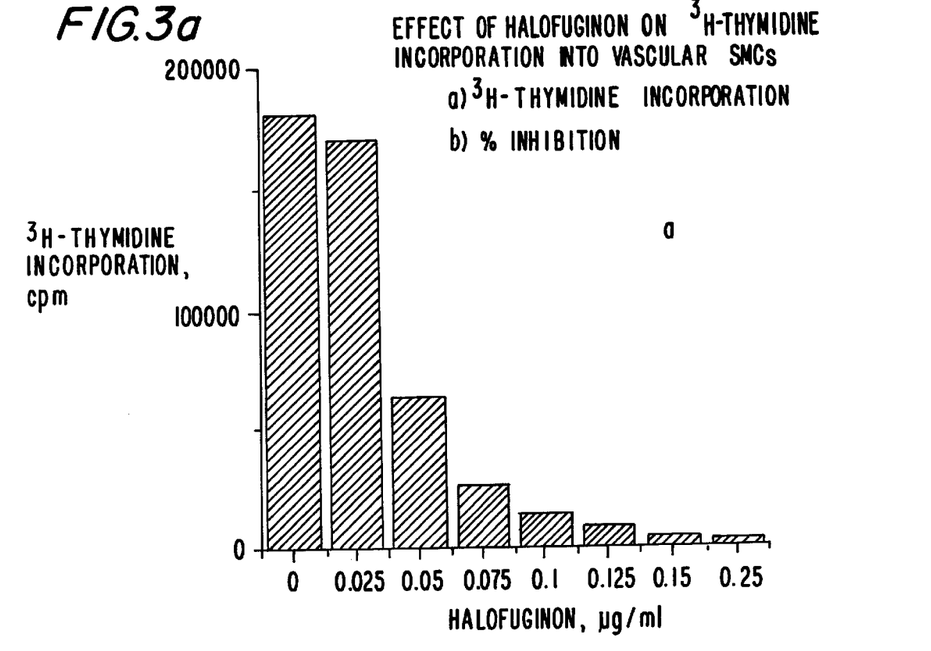
FIGS. 3a and 3b respectively are a bar graph and a characteristic curve, showing the effect of halofuginone on $^3$H-thymidine incorporation into vascular SMCs.
Figure 3B:
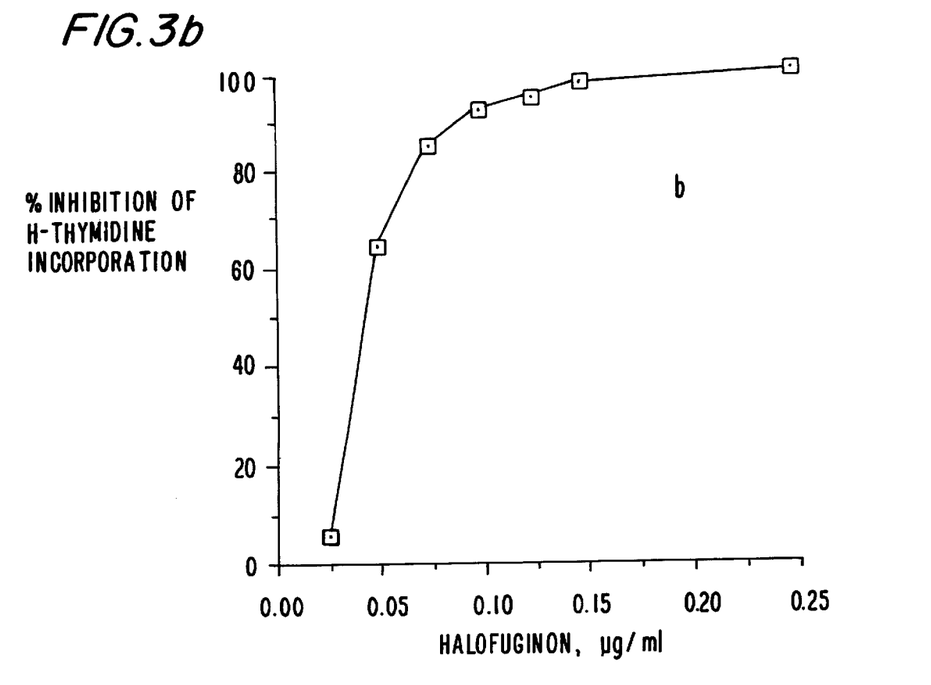
Figure 4:
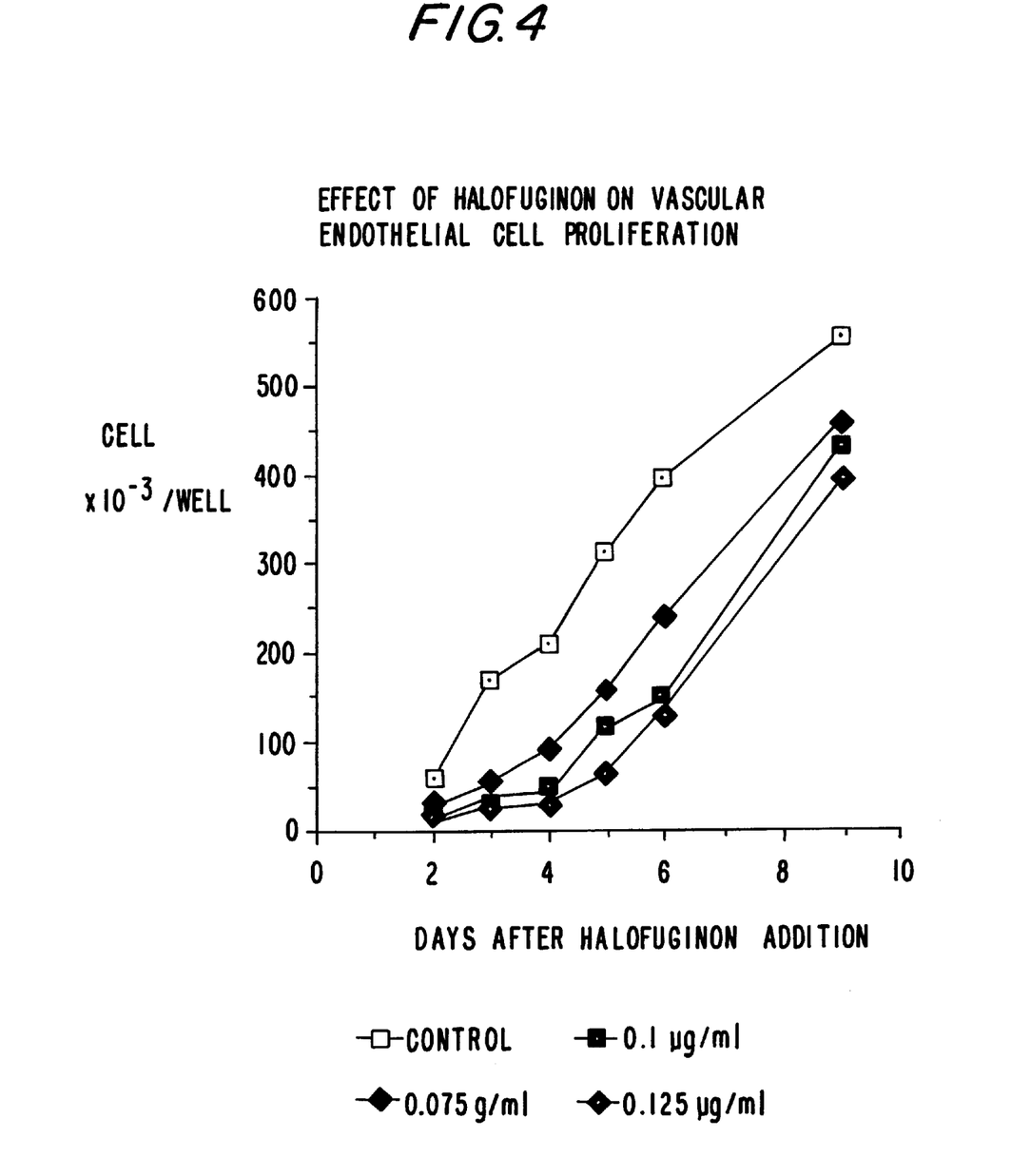
FIG. 4 is a characteristic curve showing the effect of halofuginone on vascular endothelial cell proliferation.
Figure 5A:
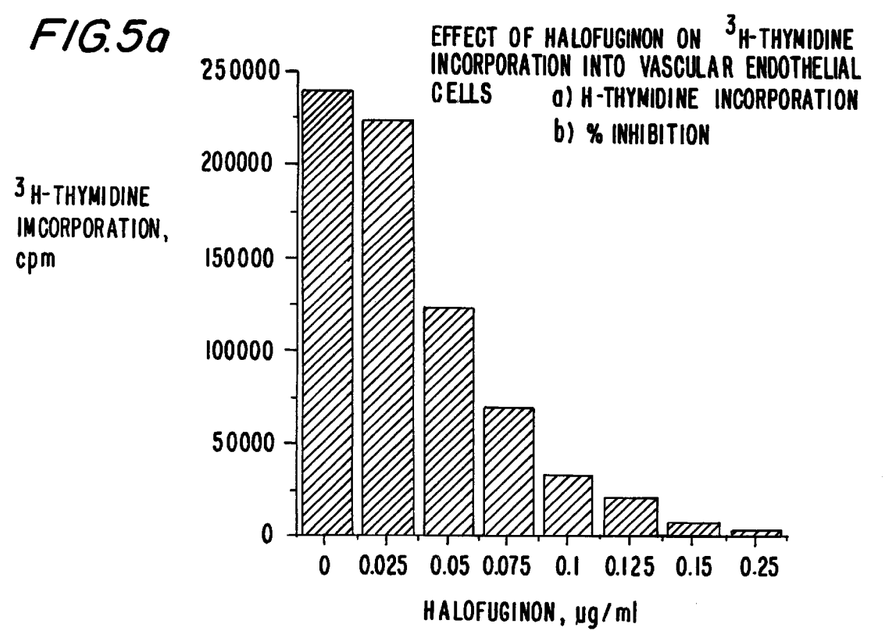
FIGS. 5a and 5b respectively are a bar graph and a characteristic curve, showing the effect of halofuginone on $^3$H-thymidine incorporation into vascular endothelial cells.
Figure 5B:
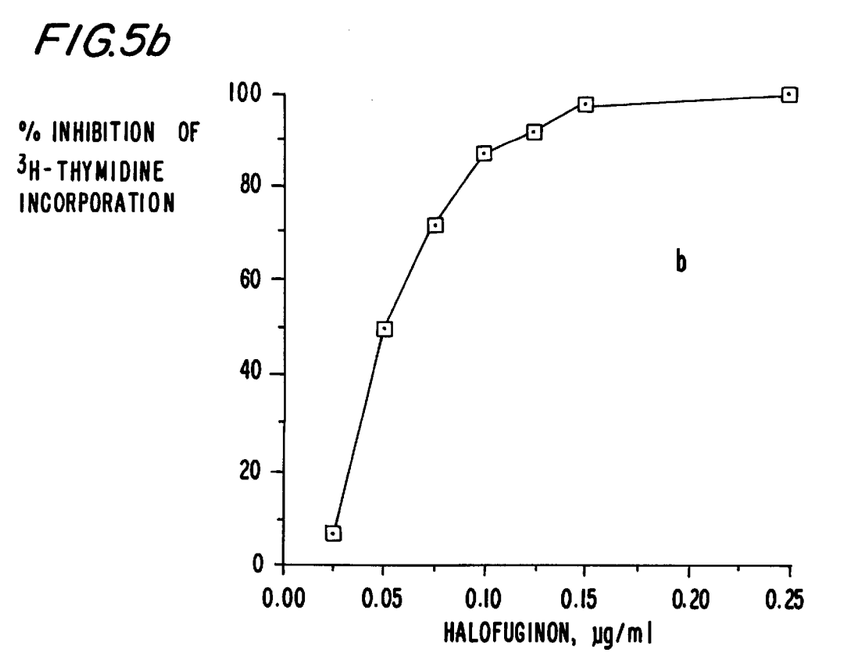

Subconfluent vascular SMCs maintained in a medium containing 10% FCS were exposed (48 hours, 37 dC) to $^3$H-thymidine in the absence and presence of increasing concentrations of halofuginone. As demonstrated in FIG. 3a, complete inhibition of DNA synthesis was observed at 0.15 mg/ml halofuginone, while 65% inhibition was obtained at a concentration as low as 0.05 mg/ml (FIG. 3b).

ii) Antiproliferative Effect toward Vascular Endothelial Cells and 3T3 Fibroblasts Vascular Endothelial Cells Sparsely seeded bovine aortic endothelial cells were cultured in medium containing 10% CS in the absence and presence of increasing concentrations of halofuginone. The cells were dissociated with STV and counted daily. Inhibition of endothelial cell proliferation was observed primarily during the first 4 days, in cells treated with relatively high concentrations (0.1–0.125 mg/ml) of the drug (FIG. 4). Unlike the results with SMCs, the endothelial cells regained an almost normal growth rate (doubling time), starting on day 5 (FIG. 4), indicating that vascular EC are less susceptible than vascular SMCs to the inhibitory effect of halofuginone. Thymidine incorporation studies revealed a 50% inhibition of DNA synthesis at 0.05 mg/ml halofuginone (FIG. 5).

3T3 Fibroblasts

Figure 6:
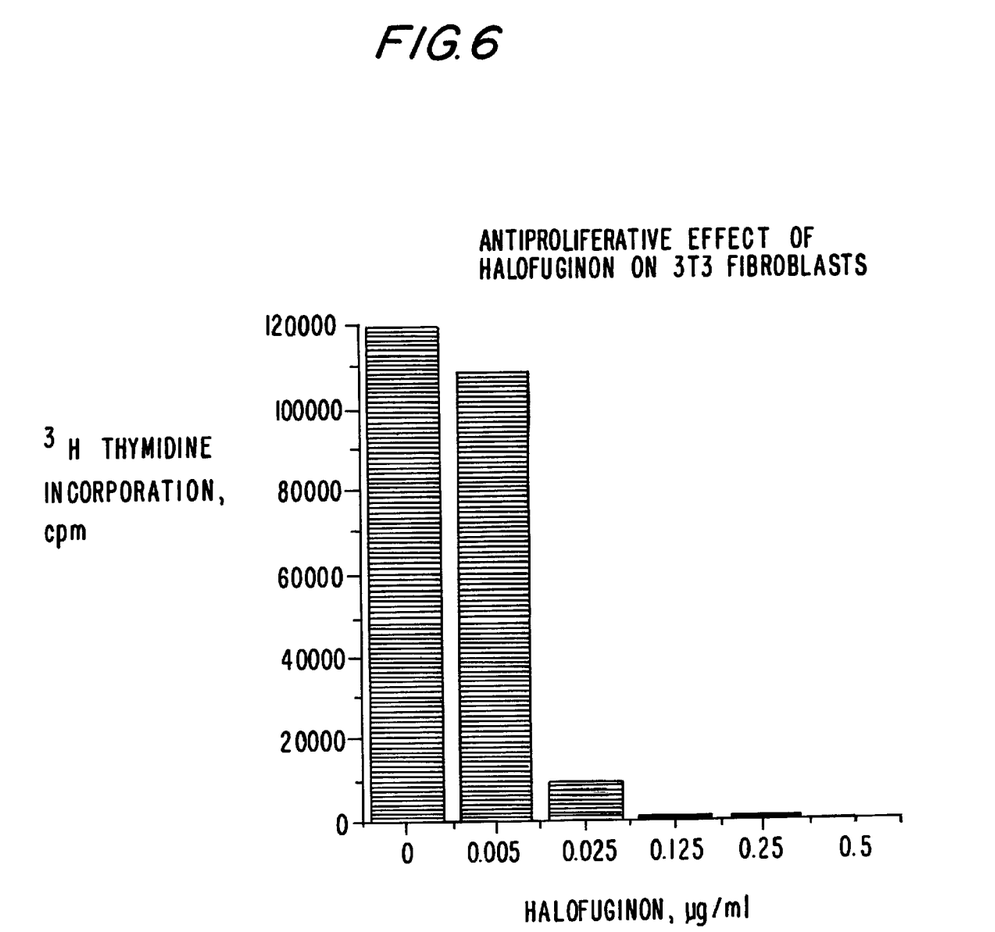
FIG. 6 is a bar graph showing antiproliferative effect of halofuginone on 3T3 fibroblasts.

FIG. 6 demonstrates that $^3$H-thymidine incorporation by actively growing 3T3 fibroblasts maintained in medium containing 10% FCS was almost completely inhibited in the presence of 0.025 mg/ml halofuginone, suggesting that fibroblasts are even more sensitive to the drug as compared to SMCs.

Effect on bFGF-Induced Cell Proliferation

Figure 7:
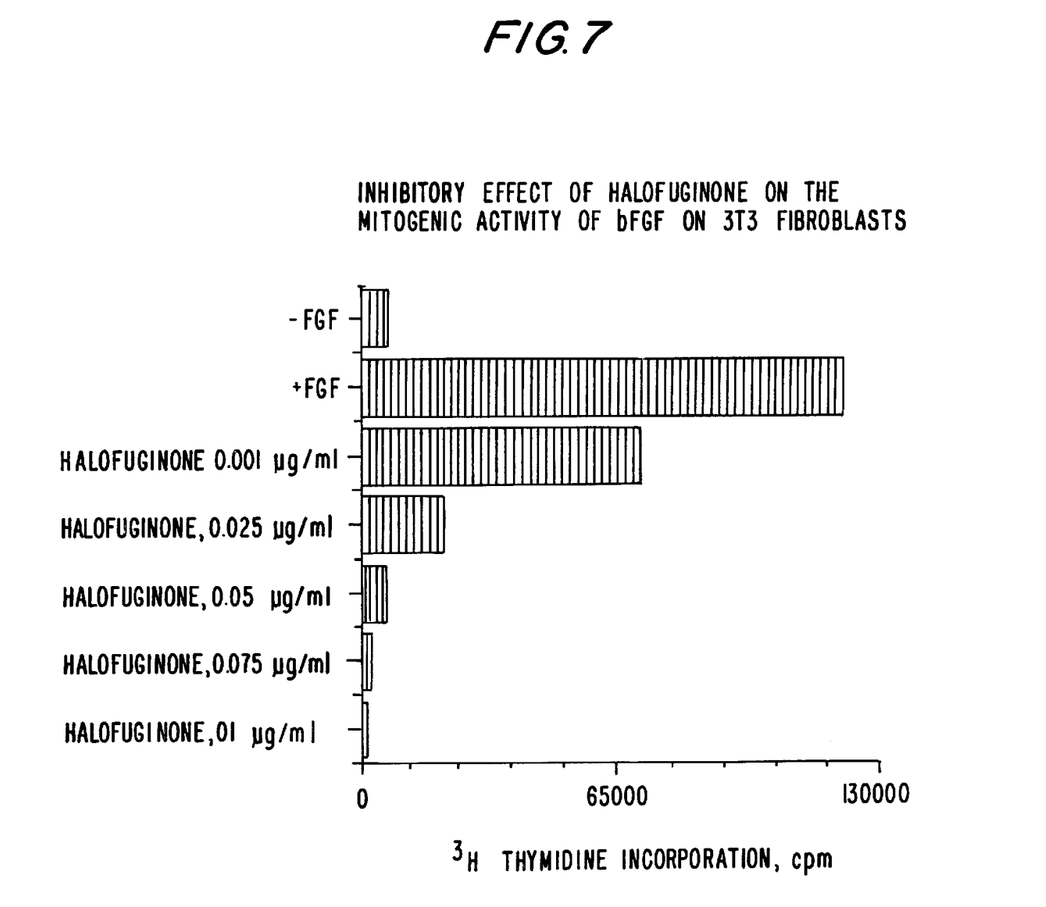
FIG. 7 is a bar graph showing the inhibitory effect of halofuginone on the mitogenic activity of bFGF.

Quiescent, growth arrested 3T3 fibroblasts maintained (48 hours) in medium containing 0.5% FCS are readily stimulated to proliferate by low concentrations at basic fibroblast growth factor (bFGF). Exposure to halofuginone (0.025 mg/ml) resulted in an almost complete inhibition of bFGF-stimulated thymidine incorporation in growth-arrested 3T3 fibroblasts (FIG. 7). This result suggests that halofuginone efficiently antagonizes the growth-promoting activity of bFGF.

iii) Arterial Stenosis Caused by Physical Injury

Adult New Zealand rabbits were anesthetized by intramuscular injection of ketamine (50 mg/kg). Physical injury was applied for 30 min. externally to the central artery of each ear [Banai, et al., *Circulation Res.*, Vol. 69, pp. 748–756 (1992)]. After the operation, the rabbits were housed in accordance with Animal Welfare Act specifications. Halofuginone (0.2 ml of 0.09 mg/ml) was introduced subcutaneously around the physical crush area 1 hour after the crush and once every 24 hours during the first 4 days. On day 14, the animals were sacrificed and the ears fixed in 10% buffered formaldehyde for 72 hours. The crush sites were further trimmed at 1 mm intervals, dehydrated in ethanol and xylene, and embedded in paraffin. Serial (5 mm) sections were stained by Movat pentachrome method. Computerized planimetry was performed at the site of the lesion and at an adjacent normal arterial segment displaced 2 mm from the location of the injury. Selection of the normal site was random; approximately one-half were proximal and one-half distal to the injury site. The lumen, the area cricumscribed by the internal elastic lamina ("original lumen") and the area circumscribed by the external border of the media (total vessel area) were traced, and the ratio between neointima and media was calculated. In all cases, the single section demonstrating the greatest extent of neointimal proliferation was selected for planimetry.

Figure 8A:
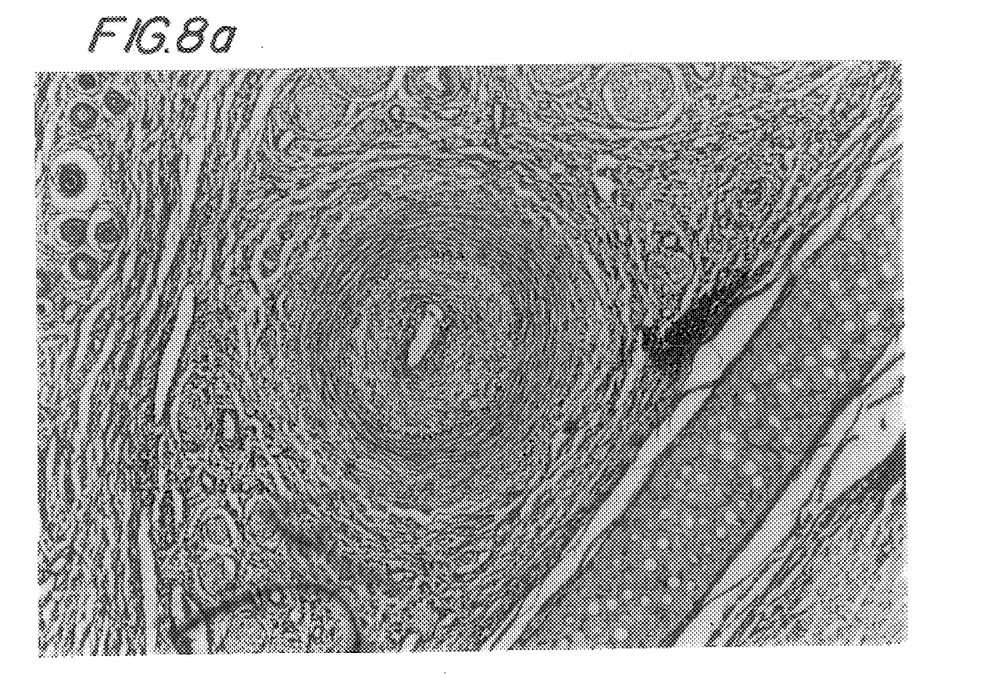
FIGS. 8a and 8b are color light micrographs of the central artery of a rabbit ear after being subjected to crush injury, respectively showing an untreated artery and an artery treated according to the present invention.
Figure 8B:
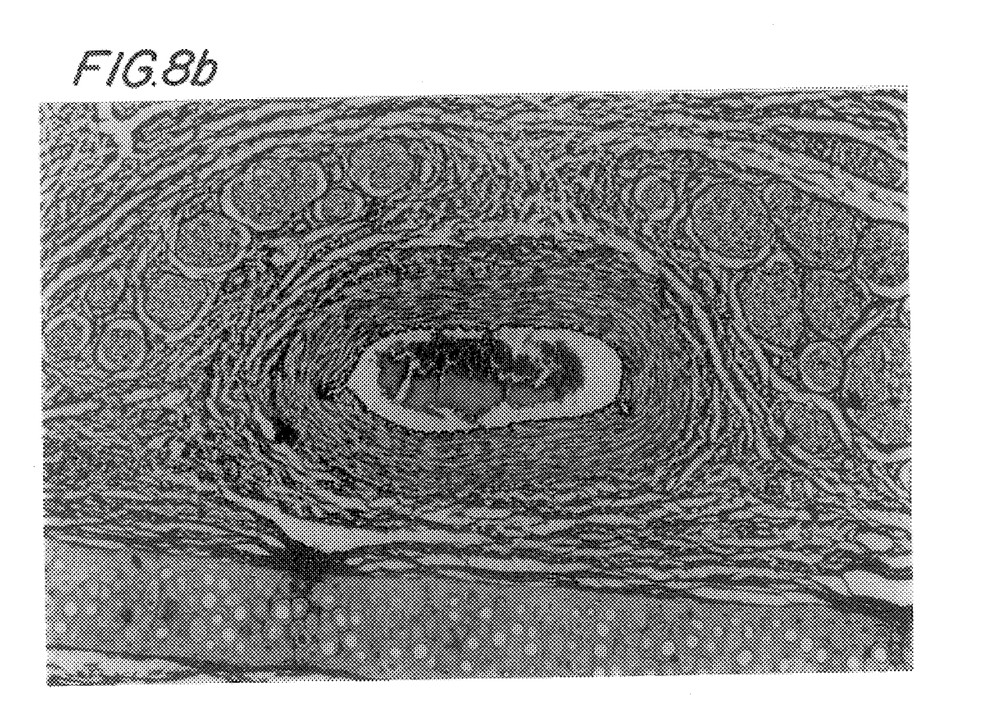

Referring now to FIGS. 8a and 8b, there are seen light micrographs of the central artery of a rabbit ear 14 days after external crush injury (Movat staining of representative cross-sections).

In FIG. 8a, the SMCs are migrating from the media into the neointima through the disrupted internal elastic lamina and the artery lumen is narrowed by the protruding neointima in the untreated artery. As can be seen, there is striking neointimal formation and an almost complete obliteration of the arterial lumen.

In contradistinction, in FIG. 8b there is seen a rabbit ear artery subjected to crush injury and treatment with halofuginone. An almost complete inhibition of neointimal formation is observed.

Figure 9:
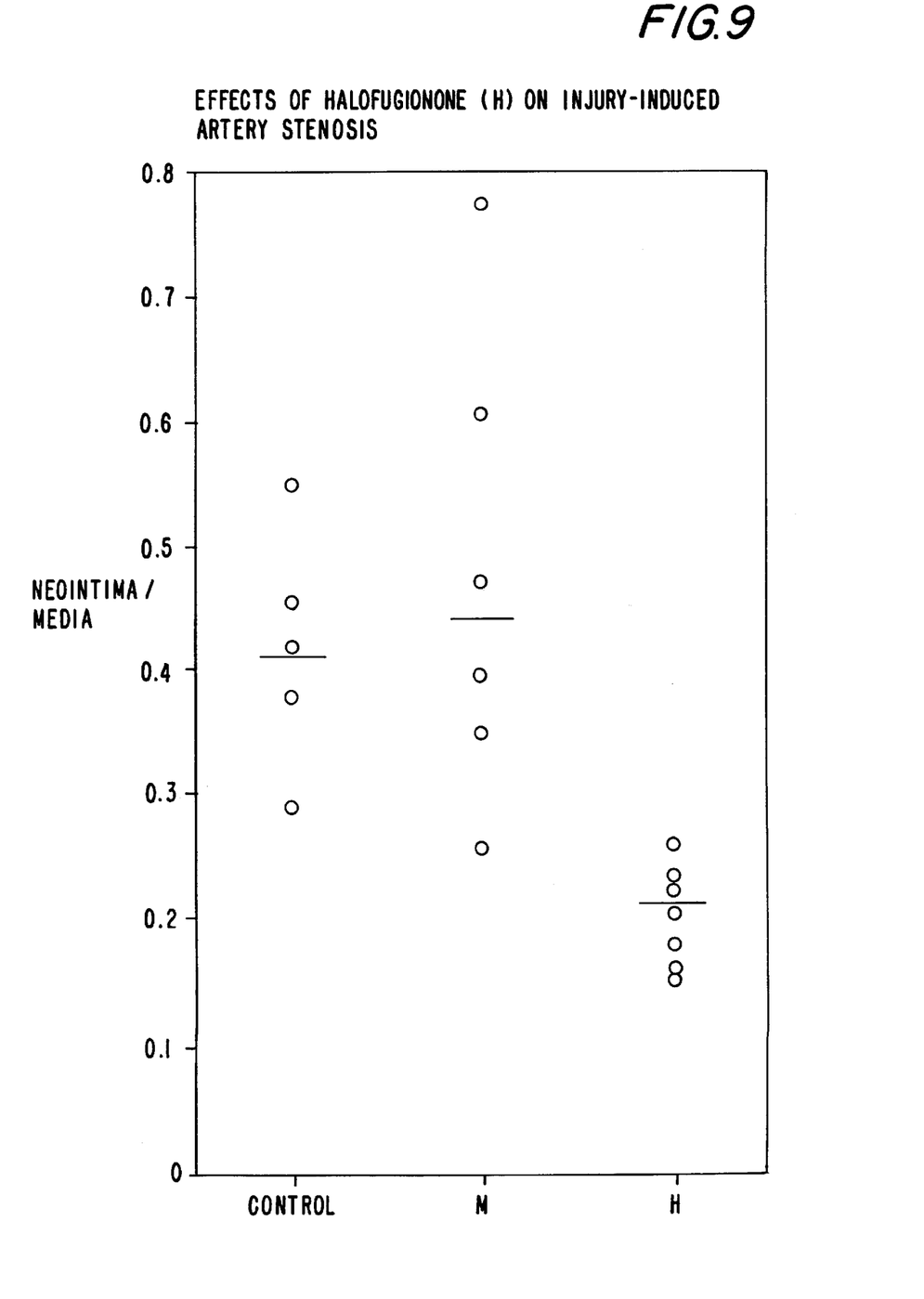
FIG. 9 is a graph showing the effect of halofuginone on injury-induced artery stenosis.

FIG. 9 shows a quantitative analysis of the ratio between neointima to media performed in control rabbits and rabbits treated with halofuginone (H) or a synthetic heparin-mimicking compound (M). Each point represents one rabbit.

As stated hereinbefore, quinazolinone derivatives of formula I, and preferably halofuginone, are incorporated in a polymeric matrix coating of the metal stent. The drug is dispersed or dissolved in a polymeric solution or melt and applied onto a metal stent by dripping or spray process. The following examples demonstrate the release of halofuginone from a polymeric coating. It is to be noted that the polymeric coating is chosen not to affect the normal performance of the stent, such as the expansion of the stent in application or deformation of the polymeric coating during its presence within the blood vessel.

Example 1

Coating of a Metal Stent with a Polymeric Matrix

A solution of polyethylene vinyl acetate (EVA, 1% w/w in dichloromethane) and 0.1 wt % of halofuginone free base is prepared. The desired stent is dipped once into the EVA-drug solution and the stent is allowed to dry at room air to yield a smooth uniform coating of about 10 microns thickness. If thicker coating is desired, the dipping process is repeated several times. To improve the adherence of the EVA coating on the stent, the stent is pre-treated with a prime polymer coating that allows adhesion of the EVA coating. The coating is flexible and does not affect the expandability of the stent. The concentration of the polymer and drug may vary from 0.1% to about 10% of polymer concentration and the drug content may vary from 1 to about 20% per polymer weight. The thickness of the coating can be varied by either the number of coating or the polymer concentration in the dipping solution.

The polymer carrier can be any pharmaceutically acceptable biopolymer that is non-degradable and insoluble in biological mediums, has good stability in a biological environment, has a good adherence to the selected stent, is flexible, and that can be applied as coating to the surface of a stent, either from an organic solvent, or by a melt process. The hydrophilicity or hydrophobicity of the polymer carrier will determine the release rate of halofuginone from the stent surface. Hydrophilic polymers, such as copolymers of hydroxyethyl methacrylate-methyl methacrylate and segmented polyurethane (Hypol), may be used. Hydrophobic coatings such as copolymers of ethylene vinyl acetate, silicone colloidal solutions, and polyurethanes, may be used. The preferred polymers would be those that are rated as medical grade, having good compatibility in contact with blood. The coating may include other antiproliferative agents, such as heparin, steroids and non-steroidal anti-inflammatory agents. To improve the blood compatibility of the coated stent, a hydrophilic coating such as hydromer-hydrophilic polyurethane can be applied.

Example 2

Halofuginone Release from Polymer Coating

The releasee of drug from the stent coating is determined in vitro by placing the device into a large volume of physiologic solution (0.1 M phosphate buffer, pH 7.4) at 37° C. The drug release to the solution is periodically determined by HPLC. For the coating described in Example 1 (single dipping of a 1% polymer solution and 10% of halofuginone per polymer weight in EVA), there was a release of about 5 to 10 mcg/cm$^2$/day for a period of 3 weeks. When a rate-limiting coating is applied, an additional dipping of the stent in a solution of 0.5% EVA containing between 0 and 5% of halofuginone is applied. The drug release rate is decreased to about 20% of the release without the rate-controlling membrane, than coated with a drug-free coating. In addition, there is no burst release and the drug is released at a constant rate for a longer time period.

The drug release profile and the duration of drug releasee can be altered by altering the coating thickness, the polymer carrier, the drug content in the polymer, composition of the coating (hydrophilic or hydrophobic additives; blends of polymers), the drug content within the various layers of coating, the configuration of the stent, and the properties of the rate-controlling membrane. It is possible to gain an adequate effect by coating the stent at specific sites such as on the outer surface only (can be chieved by either selected spray coating or by shielding the inner side of the stent) or coating certain parts of the stent, such as the edges.

Conclusions

Current approaches to inhibit the proliferation of vascular SMC utilize heparin, suramin, antibodies to various growth-promoting factors, anti-thrombin agents, and, most recently, antisense DNA technique. Heparin is a potent anticoagulant and its anti-proliferative activity is relatively small and subjected to major variations depending on the source and manufacturing company. Suramin is highly toxic at the effective dose, while antibodies are expensive, have a short half life and may elicit an immune response. Information on the antisense approach is new, and at present very limited.

The present invention, in its most preferred embodiment, utilizes a highly potent, inexpensive and non-toxic compound which inhibits the activity of various growth factors, including bFGF, and inhibits autocrine growth of vascular SMC and fibroblasts. Moreover, halofuginone is a low molecular weight compound which can be administered orally. The compound has been approved by the F.D.A. for use in farm animals. These characteristics make halofuginone a most promising clinically useful drug to inhibit restenosis.

Thus, the present invention provides for the use of halofuginone as a non-toxic compound that efficiently inhibits SMC proliferation, to provide an effective strategy for inhibiting the pathophysiology of arteriosclerosis, restenosis after coronary angioplasty, and neointimal proliferation in saphenous vein grafts.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. An intracoronary stent coated with a quinazolinone derivative of formula I:

wherein:

n is 1 or 2;

$R_1$ is a member of the group consisting of hydrogen, halogen, nitro, benzo, lower alkyl, phenyl and lower alkoxy;

$R_2$ is a member of the group consisting of hydroxy, acetoxy, and lower alkoxy, and $R_3$ is a member of the group consisting of hydrogen and lower alkenoxy-carbonyl;

or with a physiologically acceptable salt thereof, in combination with a polymer carrier that is non-degradable and insoluble in biological mediums, for preventing restenosis after angioplasty.

2. A stent according to claim 1, wherein said quinazolinone derivative is halofuginone.

* * * * *